United States Patent
Shi et al.

(10) Patent No.: US 11,643,637 B2
(45) Date of Patent: May 9, 2023

(54) ESTABLISHMENT AND APPLICATION OF HUMAN IMMORTALIZED B LYMPHOCYTE CELL LINE GROUP

(71) Applicant: FUDAN UNIVERSITY, Shanghai (CN)

(72) Inventors: Leming Shi, Shanghai (CN); Yuanting Zheng, Shanghai (CN); Wanwan Hou, Shanghai (CN); Bin Li, Shanghai (CN); Xingdong Chen, Shanghai (CN); Ying Yu, Shanghai (CN); Jiucun Wang, Shanghai (CN); Li Jin, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 435 days.

(21) Appl. No.: 16/771,921

(22) PCT Filed: Nov. 9, 2018

(86) PCT No.: PCT/CN2018/114872
§ 371 (c)(1),
(2) Date: Jun. 11, 2020

(87) PCT Pub. No.: WO2019/114473
PCT Pub. Date: Jun. 20, 2019

(65) Prior Publication Data
US 2021/0087527 A1    Mar. 25, 2021

(30) Foreign Application Priority Data

Dec. 11, 2017  (CN) .......................... 201711309755.X

(51) Int. Cl.
*C12N 5/0781*    (2010.01)

(52) U.S. Cl.
CPC .................................. *C12N 5/0635* (2013.01)

(58) Field of Classification Search
None
See application file for complete search history.

*Primary Examiner* — Sharon X Wen
(74) *Attorney, Agent, or Firm* — Novick, Kim & Lee, PLLC; Allen Xue

(57) ABSTRACT

The present application provides a group of human immortalized B lymphocyte cell lines and use thereof, and specifically provides a combination of four closely related immortalized lymphocyte cell lines. The combination can be used as a reference substances for measuring the performance of a detection platform. When the four closely related immortalized lymphocyte cell lines are used as reference substances for epigenome, transcriptome, proteome, and metabolome, an intrinsic magnitude difference gradient can be formed to evaluate the sensitivity of histological detection.

15 Claims, 3 Drawing Sheets

ESTABLISHMENT AND APPLICATION OF HUMAN IMMORTALIZED B LYMPHOCYTE CELL LINE GROUP

TECHNICAL FIELD

The present invention relates to the field of biotechnology, in particular, to the establishment and application of a group of human immortalized B lymphocyte lines and their extract thereof.

BACKGROUND OF THE INVENTION

Immortalized cell line refers to a cell line that can proliferate indefinitely and continue to survive through passage after successful primary culture. Using Epstein-Barr virus (EBV) to transform peripheral blood B lymphocytes to establish an immortalized cell line is the most commonly used method for cell immortalization. Epstein-Barr virus is a herpes virus that is B-lymphophilic, belonging to the herpes virus family lymphotropic virus, and is a linear double-stranded DNA virus. After EBV infection of B lymphocytes, it causes the activation of B lymphocytes, the cells proliferate endlessly, and transform into an immortal lymphoblastoid cell line.

Since immortalized cell lines can provide cell models for various genetic diseases, immunology, and cell biology research under subculture conditions, it has been widely used in the preservation of genetic material and is used by the HapMap International Project for the preservation of genetic material.

At the same time, a large number of immortalized cell lines have been expanded. The National Institute of Standards and Technology (NIST) has used immortalized cell lines to prepare DNA in large quantities and made RM8398, a reference substance for whole genome DNA.

However, with the increase of new technology platforms for high-throughput omics testing, the requirements for the accuracy of reference substances and the coverage of omics testing technology platforms have gradually increased. For example, DNA sequencing analysis requires more consideration of haplotype results. It is also necessary to combine parents' sequencing data to obtain de-novo mutation information, so that a set of reference substances for family DNA is required. At the same time, the reliability and reproducibility of high-throughput detection technology platforms such as epigenome, transcriptome, and proteome also urgently need to be systematically evaluated. A set of different samples is needed to evaluate the relative magnitude of expression. Currently, there is a need for the method and the reference substances thereof reference substances for a high-throughput omics testing technology platform to verify its performance.

Therefore, there is an urgent need to develop a method and the reference substances thereof used to measuring the performance of the detection platform.

SUMMARY OF THE INVENTION

One aspect of the present invention provides a group of cell lines for manufacturing reference substances, which can be used to measure the performance of a detection platform. The group of cell lines consists human immortalized B lymphocyte line Fudan_D5, human immortalized B Lymphocyte line Fudan_D6, human immortalized B lymphocyte line Fudan_F7, and human immortalized B lymphocyte line Fudan_M8. Human immortalized B lymphocyte line Fudan_D5 was deposited with the China Center for Type Culture Collection (CCTCC) under accession number C2017238 on Nov. 8, 2017. Human immortalized B Lymphocyte line Fudan_D6 was deposited with the China Center for Type Culture Collection (CCTCC) under accession number C2017253 on Nov. 8, 2017. Human immortalized B lymphocyte line Fudan_F7 deposited with the China Center for Type Culture Collection (CCTCC) under accession number C2017254 on Nov. 8, 2017. Human immortalized B lymphocyte line Fudan_M8 was deposited with the China Center for Type Culture Collection (CCTCC) under accession number C2017255 on Nov. 8, 2017.

In another aspect, the invention provides a composition comprising human immortalized B lymphocyte line Fudan_D5, human immortalized B lymphocyte line Fudan_D6, human immortalized B lymphocyte line Fudan_F7 and human immortalized B lymphocyte line Fudan_M8.

In another aspect, the invention provides reference substances, which are cell extracts from the immortalized B-lymphocyte cell lines of the invention.

In some embodiments, the reference substances are DNA, or RNA, or metabolites, or proteins, that are cell extracts from the immortalized B-lymphocyte cell lines of the invention.

In some embodiments, the reference substances is selected from the group consisting of: a nucleic acid substance, a protein substance, a metabolite substance, and a combination thereof.

In some embodiments, the reference substances is of the same type.

In some embodiments, the nucleic acid reference substances comprises a DNA reference substance and/or a RNA reference substance.

In some embodiments, the reference substances comprises a first substances, a second substances, a third substances, and a fourth substances; wherein, the first substances is extracted from a human immortalized B lymphocyte line Fudan_D5, the second substances is extracted from human immortalized B lymphocyte line Fudan_D6, the third substances is extracted from human immortalized B lymphocyte line Fudan_F7, and the fourth substances is extracted from human immortalized B lymphocyte line Fudan_M8. The reference substances are DNA, RNA, proteins or metabolites, which are extracted from these cell lines.

In another aspect, the invention provides a reagent and/or kit for measuring the performance of a detection platform, wherein the reagent and/or kit comprising cell extracts of at least one cell lines or composition of the invention, or comprising reference substances of the invention.

In some embodiments, the detection platform is selected from the group consisting of a sequencing platform, a chip detection platform, a metabolite detection platform, a methylation detection platform, a transcriptome detection platform, a proteome detection platform, and a combination thereof.

In some embodiments, the detection platform is selected from the group consisting of a high-throughput DNA detection platform, a high-throughput RNA detection platform, and a combination thereof.

In some embodiments, the chip detection platform comprises a gene chip detection platform and/or a protein chip detection platform.

In another aspect, the invention provides a method for measure the performance of a detection platform, comprising the steps:

(a) providing a cell extract of at least one cell line or the composition of the invention, OR, providing the reference substance of the invention;

(b) constructing a library for the cell extract or the reference substance, thereby obtaining a sequencing library;

(c) sequencing the sequencing library of step (b) using the detection platform, thereby obtaining a sequencing result;

(d) comparing the sequencing result of step (c) with the threshold value of the cell extract or the reference substance, thereby evaluating and verifying the performance of the detection platform, the performance could be reflected by precision, accuracy, sensitivity, specificity, and/or detectable range.

In some embodiments, in step (d), comparing the sequencing result of step (c) with the threshold value of the cell extract or the reference substance, thereby the coincidence value is ≥99% (preferably ≥99.5%, more preferably, 99.974-99.980%), indicated the detection platform is accurate or qualified. If the coincidence value is <98%, indicating that the detection platform is inaccurate or unqualified.

In some embodiments, the method further comprises: (e) analyzing the STR of the reference substance, and comparing the obtained STR analysis result with the STR analysis result corresponding to the reference substance.

In some embodiments, based on the comparison result of step (e), thereby obtaining the coincidence value between the STR analysis result and the STR analysis result of the reference substance, if the coincidence value is ≥98% (preferably, ≥99%, more preferably, ≥99.5%), indicating that the detection platform is accurate or qualified, if the coincidence value is less than 96%, indicating that the detection platform is inaccurate or unqualified.

In some embodiments, the method further comprises: (f) analyzing the Mendelian error rate of the reference substance in an evaluating experiment, and comparing the obtained Mendelian error rate results with the Mendelian error rate threshold values established for the same platform.

In some embodiments, based on the comparison result of step (f), obtaining the coincidence value between the result of the Mendelian error rate and the Mendelian error rate of the reference substance, if the coincidence value is ≥95% (preferably, ≥98%, more preferably, ≥99%), indicating that the detection platform is accurate or qualified, if the coincidence value is less than 95%, indicating that the detection platform is inaccurate or unqualified.

In some embodiments, the method further comprises: (g) analyzing the methylation of the reference substance, and comparing the obtained methylation analysis result with the methylation analysis result corresponding to the reference substance.

In some embodiments, based on the comparison result of step (g), thereby obtaining the coincidence value of the methylation analysis result and the methylation analysis result corresponding to the reference substance, if the coincidence value is ≥98% (preferably, ≥99%, more preferably, ≥99.5%), indicating that the detection platform is accurate or qualified, and if the coincidence value is less than 96%, indicating that the detection platform is inaccurate or unqualified.

In some embodiments, the detection platform is sequenced by a high-throughput sequencer selected from the group consisting of: Illumina HiSeq XTEN, Illumina HiSeq 2500, Illumina HiSeq 2000, Illumina NovaSeq, MiSeq, Ion Torrent, BGISeq-500, PacBio, BioNano, Nanopore and a combination thereof.

In another aspect, the invention provides a kit comprising:

(a) a first container, and a first reference substance located in the first container, the first reference substance is extracted from a human immortalized B lymphocyte strain Fudan_D5;

(b) a second container, and a second reference substance located in the second container, the second reference substance is extracted from a human immortalized B lymphocyte strain Fudan_D6;

(c) a third container, and a third reference substance located in the third container, the third reference substance is extracted from a human immortalized B lymphocyte strain Fudan_F7; and (d) a fourth container, and a fourth reference substance located in the fourth container, the fourth reference substance is extracted from a human immortalized B lymphocyte strain Fudan_M8.

In some embodiments, the kit further comprises instructions, which record instructions for using the first reference substance, the second reference substance, the third reference substance, and the fourth reference substance for measuring the accuracy of the detection platform.

In another embodiment, the first container, the second container, the third container and the fourth container are different containers.

In another embodiment, the reference substance is selected from the group consisting of: a nucleic acid, a protein, a metabolite, and a combination thereof.

In another embodiment, the nucleic acid reference substance comprises a DNA reference substance and/or an RNA reference substance.

It should be understood that, within the scope of the present invention, the technical features specifically described above and below (such as the Examples) can be combined with each other, thereby constituting a new or preferred technical solution which needs not be described one by one.

DETAILED DESCRIPTION OF INVENTION

Figures 1, 2:
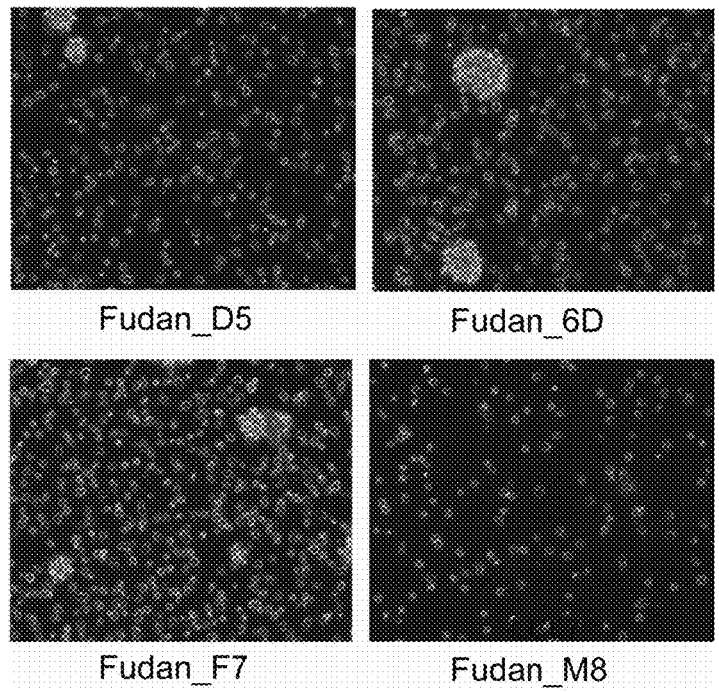
FIG. 1 shows the morphology of the immortalized B lymphocyte line (phase contrast microscope, 40×).
FIG. 2 shows the results of the STR method to identify the genetic relationship between the four cell lines and the original blood sample DNA.

After extensive and intensive research and extensive screening, the inventors have unexpectedly found that 4 immortalized B-lymphocyte lines with genetic relationships and the extracts thereof can be used reference substances for measuring the performance of the detection platform, and when 4 immortalized lymphocyte lines with genetic relationship are used as reference substance of epigenome and transcriptome, predictably, the detected results of the extract of the 4 immortalized B-lymphocyte lines should form an intrinsic magnitude difference gradient. That intrinsic magnitude of difference gradient can be used for evaluating the sensitivity of omics detection. On this basis, the inventors have completed the present invention.

Construction of cell lines for reference substances used to measure the performance of DNA sequencing platform The present invention provides cell lines for manufacturing a reference substance for measuring the performance of DNA sequencing platform. These cell lines includes a human immortalized B lymphocyte cell line Fudan_D5, a human immortalized B lymphocyte cell line Fudan_D6, human immortalized B-lymphocyte cell line Fudan_F7, human immortalized B-lymphocyte cell line Fudan_M8, and a combination thereof. The deposit number of human immortalized B-lymphocyte cell line Fudan_D5 is CCTCC NO: C2017238. The deposit number of human immortalized B lymphocyte cell line Fudan_D6 is CCTCC NO: C2017253. The deposit number of the human immortalized B lymphocyte cell line Fudan_F7 is CCTCC NO: C2017254. The deposit number of the human immortalized B lymphocyte cell line Fudan_M8 is CCTCC NO: C2017255.

The immortalized B lymphocyte lines Fudan_D5, Fudan_D6, Fudan_F7, Fudan_M8 of the present invention can be used for large-scale preparation of reference substance of DNA, RNA, protein, and metabolites, and can also be used for studying genetic relationships.

The present invention adopts the method of transfecting human B lymphocytes with EBV to obtain a set of immortalized cell lines that can be passaged stably and retain the genetic characteristics of the original blood sample. This group of immortalized B lymphocyte lines is from the family of identical twins, Fudan_D5 and Fudan_D6 are from identical twins, Fudan_F7 is from the father, and Fudan_M8 is from the mother.

The group of cell lines of the present invention has the following characteristics:

1) the genetic background is clear and the biological characteristics are stable. The immortalized cell line identified by the STR method is consistent with the original blood sample, the sequence characteristics of the whole genome thereof are more than 99.97% consistent with the original blood sample, and it remains stable after multiple passages.

2) the genetic inheritance characteristics of the identical twin 4-member family are suitable for studying the genetic relationship between offspring and parents and measuring the performance of the corresponding omics platforms.

Reference Substance

One purpose of the present invention is to provide reference substances that can measure the performance of detection platforms.

One embodiment of the present application provides a reference substances, which is extracted from the cell lines according to one aspect of the invention.

In another embodiment, the reference substances is selected from the group consisting of: a nucleic acid, a protein, a metabolite, and a combination thereof.

In another embodiment, the reference substances comprises a first reference substances, a second reference substances, a third reference substances, and a fourth reference substances, the first reference substances is extracted from a human immortalized B lymphocyte cell line Fudan_D5, the second reference substances is extracted from a human immortalized B lymphocyte cell line Fudan_D6, the third reference substances is extracted from a human immortalized B lymphocyte cell line Fudan_F7, and the fourth reference substances is extracted from a human immortalized B lymphocyte cell line Fudan_M8.

In another embodiment, the reference substances is of the same type.

In another embodiment, the nucleic acid reference substances includes a DNA reference substances and/or an RNA reference substances.

In another embodiment, the DNA reference substances includes a first DNA reference substances, a second DNA reference substances, a third DNA reference substances, and a fourth DNA reference substances, and the first DNA reference substances is extracted from a human immortalized B lymphocyte cell line Fudan_D5, the second DNA reference substances is extracted from a human immortalized B lymphocyte cell line Fudan_D6, the third DNA reference substances is extracted from a human immortalized B lymphocyte cell line Fudan_F7, and the fourth DNA reference substances is extracted from a human immortalized B lymphocyte cell line Fudan_M8.

In another embodiment, the RNA reference substances includes a first RNA reference substances, a second RNA reference substances, a third RNA reference substances, and a fourth RNA reference substances, and the first RNA reference substances is extracted from a human immortalized B lymphocyte cell line Fudan_D5, the second RNA reference substances is extracted from a human immortalized B lymphocyte cell line Fudan_D6, the third RNA reference substances is extracted from a human immortalized B lymphocyte cell line Fudan_F7, and the fourth RNA reference substances is extracted from a human immortalized B lymphocyte cell line Fudan_M8.

Methods for Measuring the Performance of a Detection Platform

The present invention provides a method for measuring the performance of a detection platform, comprising the steps:

(a) providing a reference substance according to one aspect of the present invention;

(b) constructing a library for the reference substances to obtain a sequencing library;

(c) sequencing the sequencing library of step (b) using the detection platform to be tested, thereby obtaining a sequencing result;

(d) comparing the sequencing result with the threshold value of the reference substance, thereby obtaining the performance parameters of the detection platform, including precision, accuracy, sensitivity, specificity, and/or detectable range, thereby evaluating and verifying the performance of the detection platform to be tested.

In another embodiment, in step (d), compare the sequencing result with the threshold value of the reference substances, thereby obtaining the coincidence value between the sequencing result and the threshold value of the reference substances, if the coincidence value is ≥99% (preferably, ≥99.5%, more preferably, 99.974-99.980%), indicating that the detection platform is accurate or qualified; if the coincidence value is less than 98%, indicating that the detection platform is inaccurate or unqualified.

In another embodiment, the method further includes: (e) analyzing the STR of the reference substances, and comparing the obtained STR analysis result with the STR analysis result corresponding to the reference substances.

In another embodiment, based on the comparison result of step (e), thereby obtaining the coincidence value between the STR analysis result and the STR analysis result of the reference substances, if the coincidence value is ≥98% (preferably, ≥99%, more preferably, ≥99.5%), indicating that the detection platform to be tested is accurate or qualified, if the coincidence value is less than 96%, indicating that the detection platform is inaccurate or unqualified.

In another embodiment, the method further includes: (f) analyzing the Mendelian error rate of the reference substance in an evaluating experiment, and comparing the obtained Mendelian error rate results with the Mendelian error rate threshold values established for the same platform.

In another embodiment, based on the comparison result of step (f), thereby obtaining the coincidence value between the result of the Mendelian error rate and the Mendelian error rate of the reference substances, if the coincidence value is ≥95% (preferably, ≥98%, more preferably, ≥99%), indicating that the detection platform is accurate or qualified, if the coincidence value is less than 95%, indicating that the detection platform is inaccurate or unqualified.

In another embodiment, the method further comprises: (g) analyzing the methylation of the reference substances, and comparing the obtained methylation analysis result with the methylation analysis result corresponding to the reference substances.

In another embodiment, based on the comparison result of step (g), thereby obtaining the coincidence value between the methylation analysis result and the methylation analysis result corresponding to the reference substances, if the coincidence value is ≥98% (preferably, ≥99%, more preferably, ≥99.5%), indicating that the detection platform is accurate or qualified, and if the coincidence value is less than 96%, indicating that the detection platform is inaccurate or unqualified.

In the invention, the detection platform is not particularly limited, and may be self-built by the laboratory or purchased commercially. In a preferred embodiment, the platform to be tested in the present invention is self-built by the laboratory.

The Advantages of the Present Invention Mainly Include:

(1) A group of family immortalized lymphocyte cell lines was constructed for the first time, which can produce reference substances for measuring the performance of different detection platforms. These cell lines can be passaged stably and retain the genetic characteristics of the original blood sample.

(2) When four immortalized lymphocyte lines with genetic relationships are used as reference substances for epigenome, transcriptome, proteome, and metabolome for the first time, the intrinsic magnitude differences among these cell lines, which are determined by genetic inheritance characteristics, can be used for the evaluation of the sensitivity of omics detection.

(3) The reference substances is to perform Validation on a new detection platform, laboratory, and method, and obtain a Performance Metrics, including precision, accuracy, sensitivity, specificity, detectable range, etc.

(4) To provides more information for metabolite detection platform, methylation detection platform, transcriptome detection platform, and proteome detection platform.

(5) The threshold value of reference substances for a detection platform could be determined through multiple detection repeats of the reference substances on the detection platform, then the threshold value can be determined by finding out the distribution of test data via data analysis.

The invention will be further explained below in conjunction with specific embodiments. It should be understood, these embodiments are only used to illustrate the present invention and not to limit the scope of the present invention. The experimental methods without specific conditions in the following examples are usually based on conventional conditions, such as the conditions described in Sambrook et al., Molecular Cloning: Laboratory Manual (New York: Cold Spring Harbor Laboratory Press, 1989), or according to the conditions suggested by the manufacturer. Unless otherwise specified, percentages and parts are percentages by weight and parts by weight.

Unless otherwise specified, the materials and reagents used in the examples are all commercially available products.

Example 1 Establishment of Human Immortalized B Lymphocytes

The study was approved by the Ethics Committee of the School of Life Sciences, Fudan University (Lunyan Batch No. 279), and all 4 health volunteers signed an informed consent form. 15 mL of venous blood (EDTA anticoagulation) was collected from 4 volunteers for the establishment of B lymphocyte immortalization cell lines. The four healthy volunteers were born in Taizhou, Jiangsu, a family line of identical twins.

(1) PBMC separation

Transfer 15 mL of EDTA anticoagulated whole blood to a centrifuge tube, centrifuged at 2000 rpm for 5 minutes, and separating the plasma and blood cell layer.

The blood cells after centrifugation were diluted to 30 ml with PBS, mixed well, and slowly added to the top of the Ficoll separation solution. Centrifuged at 2000 rpm for 20 minutes. Using a pipette to first remove the upper liquid, and then carefully aspirate the white blood cells, and transfer it to a new centrifuge tube.

Adding PBS to 30 ml, mixed upside down, centrifuged, and repeated three times.

(2) Naïve B cell sorting

Preparing Sorting buffer (PBS without calcium and magnesium ions+2% FBS+1 mM EDTA). The Naïve B cell sorting test was carried out according to the operation steps of EasySep™ Human Naïve B Cell Enrichment Kit (STEMCELL™, Catalog #19254).

(3) EBV infection

Washing the sorted Naïve B cells with PBS once, counting them, and resuspending the cells with complete medium containing virus (the amount of EBV virus was 10-20% of the total volume) according to the count results, the cell number was 1×105/200 μL/well (48-well plate). Centrifugation and infection were performed at 2000 rpm for 1 hour, and then it was placed in an incubator for culture.

As shown in FIG. 1, the successfully transfected cells grow in suspension in clusters, in line with the typical characteristics of EBV transfected B lymphocytes.

Example 2 Identification of the Source of the Cell Line Using STR Method

Short tandem repeat (STR), also known as microsatellite DNA, is a class of DNA sequence formed by tandem repeats with 2-6 base pairs as the core unit. Since the number of core unit repeats is highly variable and abundant among individuals, it constitutes the genetic polymorphism of the STR locus. It is the second-generation genetic marker after restricted fragment length polymorphism (RFLP) and can be used for family identification of identical twins.

(1) Purification of blood sample DNA

Using the original blood sample of the volunteers before the establishment of the line, adding 20 μL proteinase K and 50 μL anticoagulant blood into a 1.5 mL EP tube, making up the total volume to 220 μL with PBS, and proceeding to step 2.

Adding 200 μL Buffer AL, mixed well, and placed in a 56° C. water bath for 10 min.

Adding 200 μL of ethanol (96-100%) to the above sample and mixed well.

Transferring the above liquid to the purification column (DNeasy Mini spin column) and placing it in the 2 ml collection tube provided by the kit. Centrifuged at 6000 g (or 8000 rpm) for 1 min. Discarding the waste liquid and collection tube.

Putting the purification column into a new 2 ml collection tube, adding 500 μL Buffer AW1, and centrifuged at 6000 g (or 8000 rpm) for 1 min. Discarding the waste liquid and collection tube.

Putting the purification column in a new 2 ml collection tube, adding 500 μL Buffer AW2, and centrifuged at 20000 g (or 14000 rpm) for 3 min. Discarding the waste liquid and collection tube.

Putting the purification column in a new 1.5 ml or 2 ml centrifuge tube, adding 200 μL of Buffer AE, dropping it directly on the white membrane in the middle, placed at room temperature for 1 min, and centrifuged at 6000 g (or 8000 rpm) for 1 min to elute DNA.

The eluted DNA was quantified with Nanodrop, and the sample was diluted to a concentration of 10 ng/μL, and 10 μL was taken for STR detection.

(2) Purification of cell line DNA

The Fudan_D5, Fudan_D6, Fudan_F7, Fudan_M8 cells were centrifuged at 300 g for 5 min, and resuspended in 200 μL PBS solution. 20 μL proteinase K was added.

Adding 200 μL Buffer AL. Mixed well and placed in a 56° C. water bath for 10 min.

Adding 200 μL of ethanol (96-100%) to the above sample, and make sure that the ethanol and sample were thoroughly mixed.

Transferring the liquid from the above steps to the purification column (DNeasy Mini spin column) and placed in the 2 ml collection tube provided in the kit. Centrifuged at 6000 g (or 8000 rpm) for 1 min. Discarding the waste liquid and collection tube.

Putting the purification column into a new 2 ml collection tube, adding 500 μL Buffer AW1, and centrifuged at 6000 g (or 8000 rpm) for 1 min. Discarding the waste liquid and collection tube.

Putting the purification column into a new 2 ml collection tube, adding 500 μL Buffer AW2, and centrifuged at 20000 g (or 14000 rpm) for 3 min. Discarding the waste liquid and collection tube. Make sure that the membrane of the purification column has been spin-dried, because residual ethanol will interfere with subsequent reactions.

Putting the purification column in a new 1.5 mL or 2 mL centrifuge tube (provided by yourself), adding 200 μL of Buffer AE, dropping it directly on the middle white membrane, placed at room temperature for 1 min, then centrifuged at 6000 g (or 8000 rpm) for 1 min to elute DNA.

The eluted DNA was quantified with Nanodrop, and the sample was diluted to a concentration of 10 ng/μL, and 10 μL was taken for STR detection.

(3) STR detection Selecting 16 STR locus for identification of identical twins family, including: CSF1PO, D13S317, D16S539, D18S51, D19S433, D21S11, D2S1338, D3S1358, D5S818, D7S820, D8S1179, FGA, THO1, TPDX, vWA, and designing the corresponding primers for subsequent PCR verification.

PCR amplification: completing fluorescent PCR according to the designed experimental scheme, and using agarose electrophoresis to detect the results;

On-board detection: PCR products were detected by capillary electrophoresis using ABI 3730XL sequencing instrument to obtain data on the size of amplified fragments. Using GeneMarker v1.9 to process and analyze the collected data, converting the size and quantity of product fragments into intuitive and accurate waveform maps, and performing genetic analysis to get the results of genetic relationship.

FIG. 2 shows the results of genetic relationship of Fudan_D5, Fudan_D6, Fudan_F7, Fudan_M8 identified by the STR method. The 16 STR locus such as CSF1PO are all human genetic markers. Based on existing data and DNA analysis results, it is supported that Fudan_F7 and Fudan_M8 are the biological parents of Fudan_D5 and Fudan_D6, and Fudan_D5 and Fudan_D6 are identical twins. In addition, the DNA of the cell line is consistent with the identification results of DNA of the volunteer's original blood sample.

Example 3 Comparison of DNA from Cell Lines and Original Blood Samples

The Illumina HiSeq XTen whole-genome detection platform was used to perform whole-genome sequencing on the DNA of volunteers' original blood samples and cell lines, and to evaluate the influence of the establishment process on the whole genome sequence.

(1) Method of library constructing

The library was constructed using TruSeq Nano DNA Library Prep Kit, according to the method of TruSeq DNA Sample Preparation Guide (Illumina, 15026486 Rev. C).

(2) Sequence determination

Using paired-end 150 bp sequencing, the average sequencing depth is 45×. The sequencing reagent adopts HiSeq XTen Reagent Kit v2.5.

(3) Bioinformatics analysis

After the quality control of the original sequencing data, bwa-mem was used for sequence alignment (mapping). The reference genome used was hg19, and the alignment results were preprocessed by GATK (mainly including eliminating the influence of excessive PCR and re-alignment and correction of indel mutations, base correction, etc.) and variant calling was performed by using HaplotypCaller. Two variant detection modes were used for each sample:

conventional variant detection (VCF results, only sites that were inconsistent with the reference genome were reported) and gVCF results (all sites were reported). Then, the consistency of the original blood sample and the whole genome site of the cell line was counted. Among them, the number of inconsistent sites was counted using the VCF results of the original blood sample and cell line, and the number of detectable sites was counted using the gVCF results of the original blood sample and cell line.

The results are shown in Table 1. The consistency between Fudan_D5, Fudan_D6, Fudan_F7, Fudan_M8 and the corresponding original blood sample whole genome locus is 99.976%, 99.980%, 99.974%, 99.977%, respectively.

TABLE 1

Consistency results of the whole genome sequence of the immortalized cell line and the original blood sample

| Cell line | Number of sites inconsistent with blood sample | Number of detectable sites | Consistency rate (%) |
| --- | --- | --- | --- |
| Fudan_D5 | 87,505 | 359,719,460 | 99.976 |
| Fudan_D6 | 87,445 | 427,124,551 | 99.980 |
| Fudan_F7 | 87,660 | 337,853,423 | 99.974 |
| Fudan_M8 | 87,946 | 386,291,050 | 99.977 |

Example 4 Effect Analysis of Quadruple Reference Substances VS Triple Reference Substances In this example, in order to compare the detection effects of the quadruple reference substances and the triple reference substances, identical twin families were used as genomic reference substances to perform Mendelian genetic error analysis.

Methods were Shown as Below:

Using the Illumina HiSeq XTen whole-genome detection platform, whole genome sequencing was performed for the DNA of the four cell lines. The sequencing errors were evaluated according to the Mendelian genetic rules of the family, and comparing the advantages of the detection rate of sequencing errors in identical twin families over the detection rate of ordinary families of three.

(1) Method of library constructing

The library was constructed using TruSeq Nano DNA Library Prep Kit, according to the method of TruSeq DNA Sample Preparation Guide (Illumina, 15026486 Rev. C).

(2) Sequence determination

Using paired-end 150 bp sequencing, the average sequencing depth is 45×. The sequencing reagent adopts HiSeq XTen Reagent Kit v2.5.

(3) Bioinformatics analysis

After the quality control of the original sequencing data, bwa-mem was used for sequence alignment (mapping). The reference genome used was hg19, and the alignment results was preprocessed by GATK (mainly including eliminating the influence of excessive PCR and re-alignment and correction of indel mutations, base correction, etc.) and the variant calling was performed by using HaplotypCaller. Two variant detection modes were used for each sample: conventional variant detection (VCF results, only sites that were inconsistent with the reference genome were reported) and gVCF results (all sites were reported). Then, the consistency of the original blood sample and the whole genome site of the cell line was counted. Among them, the number of inconsistent sites was counted using the VCF results of the original blood sample and cell line, and the number of detectable sites was counted using the gVCF results of the original blood sample and cell line.

The results are shown in Table 2. Trio1 is the threshold value of Mendelian genetic error rate calculated with Fudan_D5, Fudan_F7, Fudan_M8, Trio2 is the threshold value of Mendelian genetic error rate calculated with Fudan_D6, Fudan_F7, Fudan_M8, and the independently detected Mendelian genetic error rates of the Trio1 and Trio2 families of the three technical duplication families are all between 0.33 and 0.35%. The quadruple reference substances as the identical twin family (Quartet) not only can detect the Mendelian genetic error rate detected by triple reference substances, such as Trio1 and Trio2, but also can detect the inconsistency of genotypes loci between Fudan_D5 and Fudan_D6. The latter situation meets the genetic rules of Trio1 and Trio2, respectively, but so cannot be detected by triple reference substances. In this example, a Mendelian genetic error rate of 0.9%, also set as a threshold value, can be detected.

TABLE 2

| | Number of detectable sites | | | | | Error rate(%) | | | |
|---|---|---|---|---|---|---|---|---|---|
| | Total | Fudan_D5 | Fudan_D6 | Fudan_F7 | Fudan_M8 | Trio1 | Trio2 | Quartet | Ti/Tv |
| 1 | 6,503,734 | 4,840,979 | 4,836,825 | 4,814,322 | 4,827,198 | 0.33 | 0.35 | 0.87 | 1.98 |
| 2 | 6,512,814 | 4,846,926 | 4,846,390 | 4,822,709 | 4,843,043 | 0.36 | 0.36 | 0.92 | 1.98 |
| 3 | 6,512,489 | 4,839,350 | 4,847,558 | 4,814,966 | 4,835,124 | 0.35 | 0.35 | 0.90 | 1.98 |

The results show that it can be seen from Table 4 that when the triple reference substances are used, their detection rate for Mendelian inheritance is only between 0.33 and 0.35%, and when the quadruple reference substances are used, they increase the detection rate of Mendelian inheritance by about 200%, which can reflect that the data can be mutually verified by adding quadruple reference substances, thereby more effectively detecting more Mendelian genetic errors. This suggests that the quadruple reference substances of the present invention can provide more mutual verification information when evaluating the capabilities and detection performance of the detection platform, to enable a more comprehensive evaluate of the performance indicators of the detection platform, including: precision, accuracy, sensitivity, specificity, detectable range.

In addition, it can be seen from the above that a synergistic detection effect can be achieved more effectively.

Example 5 Evaluation on the Quality of Methylation Detection Chip by Quadruple Reference Substances In this example, when identical twin families were used as reference substances for epigenome, transcriptome, proteome, and metabolome, the intrinsic magnitude differences among individuals, which are determined by genetic inheritance characteristics, can be used to evaluate the sensitivity of omics detection.

In this example, DNA reference substances were used to detect differences in methylation of identical twin families.

Methylation Detection:

Reference substances at the epigenome, transcriptome, proteome, metabolome and other levels of identical twin families, and their intrinsic magnitude differences, that is, Fudan_D5 and Fudan_D6 were more similar in terms of epigenome, transcriptome, proteome, metabolome, etc., and the magnitude difference was smaller than the difference between that and Fudan_F7 and Fudan_M8. This inherent difference in magnitude of identical twins was innovative in evaluating the quantitative accuracy of technical platforms such as epigenome, transcriptome, proteome, and metabolome, etc.

Figure 3:
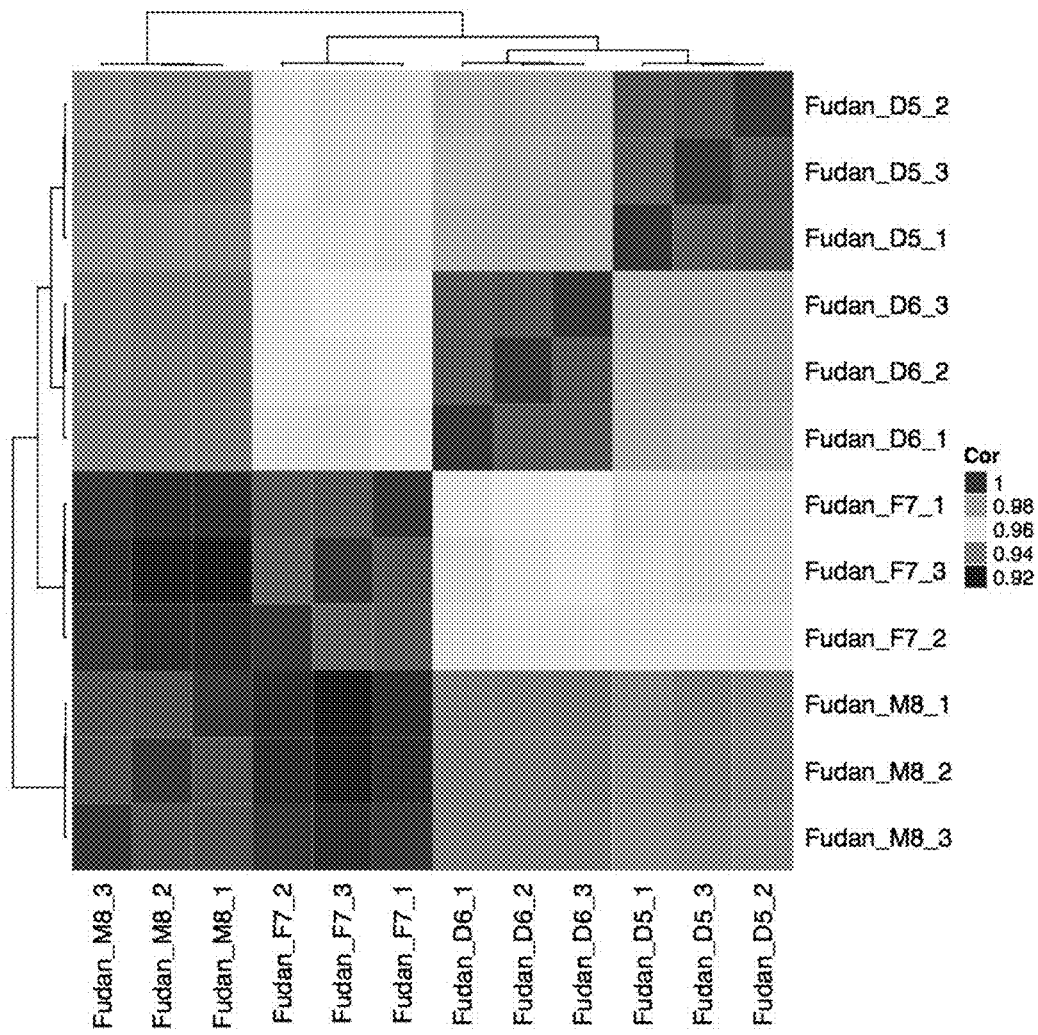
FIG. 3 shows the cluster diagram of the methylation level of 4 immortalized cell lines detected by the Illumina850K methylation chip.

FIG. 3 shows that the DNA samples of Fudan_D5, Fudan_D6, Fudan_F7, and Fudan_M8 are tested using Illumina Methylation 850K chip for 3 technical replicates, respectively. The Heatmap results show that from the methylation level, Fudan_D5 and Fudan_D6 have the highest similarity, and followed by Fudan_F7, Fudan_M8, and also show high coincidence value. This result shows that the Illumina Methylation 850K chip has high technical reproducibility and can well detect differences in methylation of identical twins.

The results in FIG. 3 show that at the DNA methylation level, three technical replicates for each of the quadruple reference substances can obtain consistent clustering results, that is, Fudan_D5 and Fudan_D6 cluster first, followed by Fudan_F7 and Fudan_M8. This result shows that the quadruple reference substances of the present invention have a stable intrinsic magnitude difference in DNA methylation level, and can be used to evaluate the performance of a methylation detection platform, including: precision, accuracy, sensitivity, and specificity, detectable range.

Example 6 Evaluation on RNA Transcriptome of Quadruple Reference Substances

In this embodiment, the reference substances of RNA was used to detect the difference in the expression level of the identical twin families.

Figure 4:
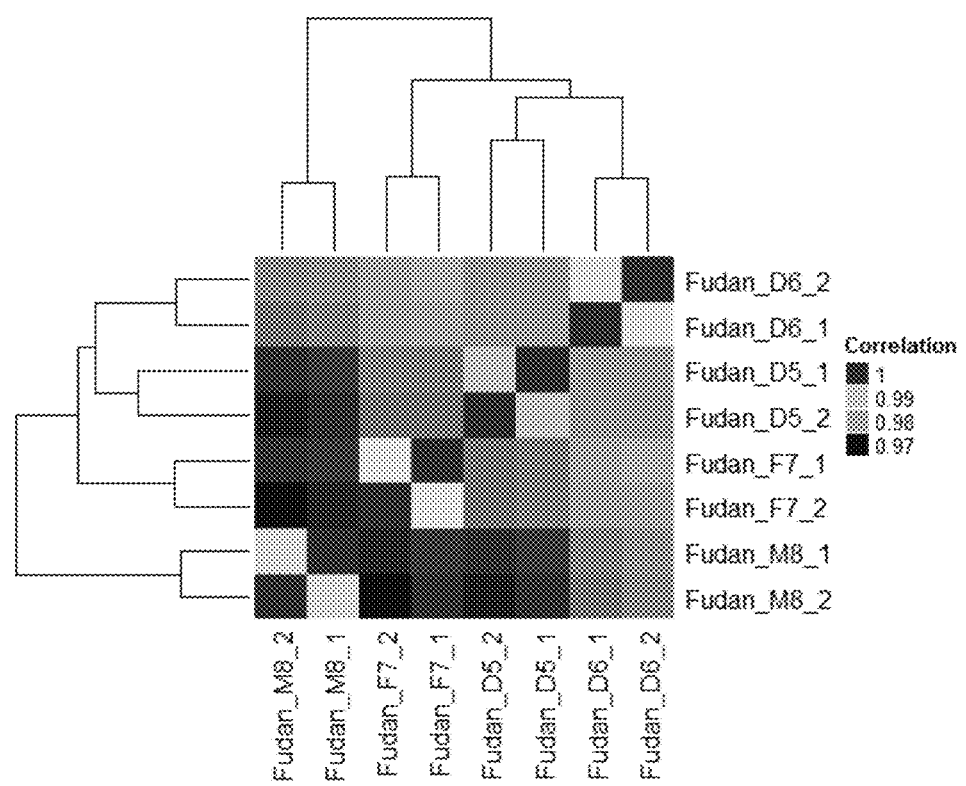
FIG. 4 shows the cluster diagram of the mRNA expression levels of 4 immortalized cell lines detected by transcriptome sequencing.

FIG. 4 is the use of Hiseq 4000, Ribo-zero library construction method to perform 2 technical replicates detection of Fudan_D5, Fudan_D6, Fudan_F7, Fudan_M8 RNA samples, respectively. Heatmap results show that Fudan_D5, Fudan_D6 have the highest similarity, followed by Fudan_F7, Fudan_M8. This result shows that RNA-Seq has high technical reproducibility and can well detect differences in the expression levels of identical twins.

The results in FIG. 4 show that at the RNA expression level, two technical duplicates for each of the quadruple reference substances can obtain consistent clustering results, that is, Fudan_D5 and Fudan_D6 cluster first, followed by Fudan_F7 and Fudan_M8, and also show high coincidence value. The results indicate that quadruple reference substances of the present invention has stable internal magnitude differences in RNA expression levels, and can be used to evaluate the performance of the transcriptome detection platform, including: precision, accuracy, sensitivity, specificity, and detectability range.

It can be seen from Examples 4, 5, and 6 that regardless of the DNA level, DNA methylation level, and RNA level, more mutually confirmed and richer information can be provided. This suggests that it is very suitable as a reference substances for a more comprehensive evaluation on testing platform, including, but not limited to: detection platform, chip detection platform, metabolite detection platform, methylation detection platform, transcriptome detection platform, proteome detection platform.

Culture Preservation

The human immortalized B lymphocyte cell line Fudan_D5 (the same as the deposit name) of the present invention has been deposited in China Center for Type Culture Collection on Nov. 8, 2017, address: Wuhan University, Wuhan, China, deposit number: CCTCC NO: C2017238.

Culture Preservation

The human immortalized B lymphocyte cell line Fudan_D6 (the same as the deposit name) of the present invention has been deposited in China Center for Type Culture Collection on Nov. 8, 2017, address: Wuhan University, Wuhan, China, deposit number: CCTCC NO: C2017253.

Culture Preservation

The human immortalized B lymphocyte cell line Fudan_F7 (the same as the deposit name) of the present invention has been deposited in China Center for Type Culture Collection on Nov. 8, 2017, address: Wuhan University, Wuhan, China, deposit number: CCTCC NO: C2017254.

Culture Preservation

The human immortalized B lymphocyte cell line Fudan_M8 (the same as the deposit name) of the present invention has been deposited in China Center for Type Culture Collection on Nov. 8, 2017, address: Wuhan University, Wuhan, China, deposit number: CCTCC NO: C2017255.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A cell line selected from the group consisting: human immortalized B lymphocyte line Fudan_D5 deposited with the China Center for Type Culture Collection (CCTCC) under accession number C2017238 on Nov. 8, 2017, human immortalized B Lymphocyte line Fudan_D6 deposited with the China Center for Type Culture Collection (CCTCC) under accession number C2017253 on Nov. 8, 2017, human immortalized B lymphocyte line Fudan_F7 deposited with the China Center for Type Culture Collection (CCTCC) under accession number C2017254 on Nov. 8, 2017, and human immortalized B lymphocyte line Fudan_M8 deposited with the China Center for Type Culture Collection (CCTCC) under accession number C2017255 on Nov. 8, 2017.

2. A composition comprising: human immortalized B lymphocyte line Fudan_D5 deposited with the China Center for Type Culture Collection (CCTCC) under accession number C2017238 on Nov. 8, 2017, human immortalized B Lymphocyte line Fudan_D6 deposited with the China Center for Type Culture Collection (CCTCC) under accession number C2017253 on Nov. 8, 2017, human immortalized B lymphocyte line Fudan_F7 deposited with the China Center for Type Culture Collection (CCTCC) under accession number C2017254 on Nov. 8, 2017, and human immortalized B lymphocyte line Fudan_M8 deposited with the China Center for Type Culture Collection (CCTCC) under accession number C2017255 on Nov. 8, 2017.

3. A reference substance, which is extracted of at least one cell line of claim 1.

4. The reference substance of claim 3, wherein the reference substance is selected from the group consisting of: DNA, RNA, metabolites, or proteins.

5. A method for measuring the performance of a detection platform, comprising the steps:
(a) providing a reference substance of claim 3 and a detection platform;
(b) constructing a library for the reference substance, thereby obtaining a sequencing library;
(c) sequencing the sequencing library of step (b) using the detection platform, thereby obtaining a sequencing result;
(d) comparing the sequencing result of step (c) with the threshold value of the reference substance, thereby evaluating and verifying the performance of the detection platform.

6. The method of claim 5, wherein in step (d), comparing the sequencing result of step (c) with the threshold value of the reference substance to obtain a matching value, thereby the matching value is ≥99% indicated the detection platform is accurate or qualified.

7. The method of claim 6, wherein the detection platform is selected from the group consisting of: a sequencing platform, a chip detection platform, a metabolite detection platform, a methylation detection platform, a transcriptome detection platform, a proteome detection platform, and a combination thereof.

8. A kit comprising a cell extract of at least one cell line of claim 1.

9. The kit of claim 8, wherein the cell extract is selected from the group consisting of: DNA, RNA, metabolites, and proteins.

10. A kit comprising the reference substance of claim 3.

11. The kit of claim 10, wherein the reference substance is selected from the group consisting of: DNA, RNA, metabolites, or proteins.

12. A reference substance which is extracted of the composition of claim 2.

13. The reference substance of claim 12, wherein the reference substance is selected from the group consisting of: DNA, RNA, metabolites, or proteins.

14. A kit comprising a cell extract of the composition of claim 2.

15. The kit of claim 14, wherein the cell extract is selected from the group consisting of: DNA, RNA, metabolites, and proteins.

* * * * *